United States Patent
Fassbender et al.

(10) Patent No.: US 8,529,873 B2
(45) Date of Patent: Sep. 10, 2013

(54) SE-72/AS-72 GENERATOR SYSTEM BASED ON SE EXTRACTION/ AS REEXTRACTION

(75) Inventors: Michael Ernst Fassbender, Los Alamos, NM (US); Beau D Ballard, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 201 days.

(21) Appl. No.: 13/216,964

(22) Filed: Aug. 24, 2011

(65) Prior Publication Data

US 2013/0052133 A1 Feb. 28, 2013

(51) Int. Cl.
*A61K 51/00* (2006.01)
*A61M 36/14* (2006.01)

(52) U.S. Cl.
CPC ................................. *A61K 51/00* (2013.01)
USPC ........................................................ 424/1.11

(58) Field of Classification Search
CPC .............................. A61K 51/00; A61M 36/14
USPC ...................................................... 424/1.11
See application file for complete search history.

(56) References Cited

U.S. PATENT DOCUMENTS

| | | | |
|---|---|---|---|
| 5,164,095 | A | 11/1992 | Sparapany et al. |
| 5,204,072 | A | 4/1993 | Phillips |
| 5,371,372 | A | 12/1994 | Phillips |
| 5,405,589 | A | 4/1995 | Phillips |
| 5,510,040 | A | 4/1996 | Miller et al. |
| 5,987,087 | A | 11/1999 | Zhuikov et al. |
| 6,127,394 | A | 10/2000 | Pershadsingh et al. |
| 6,887,891 | B2 | 5/2005 | Harnett et al. |
| 2001/0016600 | A1 | 8/2001 | Kennedy |

OTHER PUBLICATIONS

Al-Kouraishi et al., "An Isotope Generator for 72As," The International Journal of Applied Radiation and Isotopes (1978), vol. 29, pp. 607-609.
Fassbender et al., Applied Radiation and Isotopes (2001), vol. 54, pp. 905-913.
Fassbender et al, Nuclear Instruments and Methods in Physics Research Section B: Beam Interations with Materials and Atoms (2007), vol. 261, pp. 742-746.
Gadzuric et al., "Extracting Information from the Molten Salt Database," Metall. Mater. Trans. A (2006), vol. 37A, pp. 3411-3414.
Jennewein et al., "A No-Carrier added 72se/72As Radionuclide Generator Based on Solid Phase Extraction," Radiochim. Acta (2005), vol. 93, pp. 579-583.
Phillips et al., Radioact. Radiochem. (1992), vol. 3, pp. 53-58.
Phillips et al., Radiochim. Acta, (2000), vol. 88, pp. 149-155.
Saygi et al., Talanta (2007), vol. 71, pp. 1375-1381.
Wenclawiak et al., "Studies on Bulky Residual Group Substituted Arsenic (III) Dithiocarbamate Structures," Inorg. Chim. Acta., May 2003, vol. 348, pp. 1-7.
IAEA Radioisotopes and Radioisotopes and Radiopharmaceuticals Series No. 2, 2010.
Mushtaq et al., Production of 73 SE Via (p,3n) and (d,4n) Reactions on Arsenic, (1988) vol, 39, No. 10, pp. 1085-1091.
Lebowitz et al., "Radionuclide Generator Systems" (Abstract), 1974.

*Primary Examiner* — Michael G Hartley
*Assistant Examiner* — Melissa Perreira
(74) *Attorney, Agent, or Firm* — Samuel L. Borkowsky

(57) ABSTRACT

The preparation of a $^{72}Se/^{72}As$ radioisotope generator involves forming an acidic aqueous solution of an irradiated alkali bromide target such as a NaBr target, oxidizing soluble bromide in the solution to elemental bromine, removing the elemental bromine, evaporating the resulting solution to a residue, removing hydrogen chloride from the residue, forming an acidic aqueous solution of the residue, adding a chelator that selectively forms a chelation complex with selenium, and extracting the chelation complex from the acidic aqueous solution into an organic phase. As the $^{72}Se$ generates $^{72}As$ in the organic phase, the $^{72}As$ may be extracted repeatedly from the organic phase with an aqueous acid solution.

19 Claims, No Drawings

SE-72/AS-72 GENERATOR SYSTEM BASED ON SE EXTRACTION/ AS REEXTRACTION

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates to a parent/daughter $^2$Se/$^{72}$As (selenium-72/arsenic-72) radioisotope generator.

BACKGROUND OF THE INVENTION

Positron emission tomography (PET) is used to generate high resolution images of organs and tissues of the human body. These images aid in medical treatment for a patient, and are prepared by infusing the patient with a radiopharmaceutical substance that includes a short-lived radioisotope, and then scanning the patient for gamma radiation. Briefly, the radioisotope undergoes radioactive decay as the radiopharmaceutical substance distributes within the patient's body. The radioactive decay results in positron emission. The emitted positrons are annihilated, which results in the production of gamma photons that are detected using an array of gamma detectors that encircle the patient. After a can is complete, an image is constructed by a computer using tomographic algorithms. The radiopharmaceutical substance must be used before the radioisotope undergoes so much radioactive decay that it becomes useless for the production of images.

Generators of radioisotopes for radiopharmaceutical substances are a cost effective alternative to on-site production, which typically requires a cyclotron (which is an expensive and complex apparatus), staff for operating the cyclotron and handling the radioactive targets, and a laboratory for processing the irradiated target into a generator. The most desirable generators of radioisotopes for radiopharmaceutical substances use a relatively long-lived parent radioisotope that continually produces, by its radioactive decay, a short-lived daughter radioisotope with desirable imaging or therapeutic properties. In equilibrium, both parent and daughter have the same activity, which decreases over time according to the half-life of the longer lived parent. This allows time for processing and shipment of a generator from a production site while supplying a continuing source of the daughter nuclide for use at a nuclear medicine clinic.

Radioarsenic is a useful radioisotope for radiopharmaceuticals. Radioarsenic offers four positron-emitting radioisotopes ($^{70}$As, $^{71}$As, $^{72}$As, and $^{74}$As) and three beta-emitting radioisotopes ($^{74}$As, $^{76}$As, and $^{77}$As). Thus, radioarsenic-based radiopharmaceuticals may be used as imaging agents as well as therapeutic agents. The half lives ($t_{1/2}$) of these radioisotopes range from 53 minutes to 18 days. Positron emitting radioisotopes may be used for positron emission tomography (PET) imaging, while beta emitting radioisotopes may be used in internal radiation therapy where radioactivity is brought close to a tumor.

$^{72}$As is a positron emitter with an emission rate of 88% and an energy E($\beta^+$max) of 2.5 MeV. $^{72}$As has a half life of 26 hours, which is short enough to limit the radiation dose delivered to the patient while long enough to allow for chemical modification prior to targeted delivery. Thus, $^{72}$As is suitable for PET imaging.

$^{72}$As is formed via the decay of $^{72}$Se ($t_{1/2}$=8.5 days, EC 100%). The $^{72}$Se/$^{72}$As parent/daughter generator is similar to the $^{82}$Sr/$^{82}$Rb system currently used in many nuclear medicine procedures in the United States. $^{72}$Se has been produced as a component in a mixture of radioisotopes by charged particle bombardment of a target. Common targets include arsenic, germanium, or bromine.

A variety of approaches for preparing $^{72}$Se/$^{72}$As generators have been reported. One approach involves repeated distillation of $^{72}$AsCl$_3$ from carrier added $^{72}$Se stock solutions. Another approach involves electroplating $^{72}$Se as Cu$_2$Se on Cu backings. Yet another approach involves solid phase extraction of $^{72}$Se. The first two approaches require elaborate radiochemical manipulations that render them unsuitable for rapid on-site handling by nuclear medical technicians. The third appears to be limited to very small dimensions, requires the use of high concentrations of bio-incompatible agents such as hydrofluoric acid, and uses elemental Se which requires an inert atmosphere to prevent oxidation, which may be difficult in a clinical setting.

Better methods for preparing $^{72}$Se/$^{72}$As generators remain desirable.

SUMMARY OF THE INVENTION

To achieve the foregoing and other objects, and in accordance with the purposes of the present invention, as embodied and broadly described herein, the present invention provides a method for preparing a $^{72}$Se/$^{72}$As generator. The method involves forming an acidic solution of an irradiated target of an alkali bromide in an aqueous solvent comprising hydrogen chloride and soluble bromide. The irradiated target includes $^{72}$Se and other radioisotopes of selenium. The soluble bromide from the solution was oxidized to elemental bromine, which was removed by distillation. The solvent was evaporated to provide a residue. After removing some of the acid, an acidic aqueous solution was prepared from the residue. This acidic solution includes a chelator that forms a soluble complex of $^{72}$Se. The complex was extracted from the aqueous solution into a liquid organic phase. The liquid organic phase became a $^{72}$Se/$^{72}$As generator after the extraction." in its place.

The invention is also concerned with a method for producing $^{72}$As. The method involves:

forming an aqueous acidic solution of an irradiated target of an alkali bromide, the aqueous acidic solution comprising hydrogen chloride and soluble bromide and water solvent, the irradiated target comprising radioisotopes of selenium that include $^{72}$Se, oxidizing the soluble bromide to elemental bromine, removing the elemental bromine from the solution, evaporating the water solvent to provide a residue, forming an acidic aqueous solution of the residue, the acidic aqueous solution comprising a chelator suitable for forming a soluble chelation complex with $^{72}$Se, extracting the soluble chelation complex with $^{72}$Se from the acidic aqueous solution into an liquid organic phase not miscible with the acidic aqueous solution, the liquid organic phase comprising a $^{72}$Se/$^{72}$As generator, and extracting $^{72}$As from the $^{72}$Se/$^{72}$As generator into an aqueous phase that includes a soluble chelator and contacting this aqueous solution with an anion exchanger to remove selenium from this aqueous phase.

The invention is also concerned with a $^{72}$Se/$^{72}$As generator. The generator includes a soluble form of $^{72}$Se dissolved in an organic phase. The $^{72}$Se is complexed to a chelator selected from oxalic acid, oxalate, R—COOH (a carboxylic acid), R—COO$^-$,

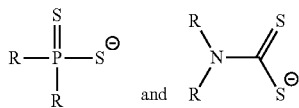

and wherein R comprises an aliphatic group, an aromatic group, or combinations thereof.

DETAILED DESCRIPTION

The invention provides a $^{72}$Se-based $^{72}$As generator. The generator may be in the form of a liquid organic phase or in the form of two phases wherein one of the phases is immobilized (i.e. one of the phases is solid). $^{72}$As may be extracted conveniently from these generators on a regular basis. These generators make $^{72}$As a readily available radioisotope to researchers and clinicians.

A generator based on a liquid organic phase was prepared from a NaBr target that had been irradiated with high energy (>80 MeV) protons. The irradiation resulted in the formation of $^{76}$Br, $^{77}$Br, $^{72}$Se, $^{75}$Se, $^{72}$As, $^{73}$As, $^{74}$As, and other radioisotopes. The target was dissolved in water. Hydrochloric acid was added, and then an aqueous 30% solution of hydrogen peroxide was added. The addition of peroxide resulted in oxidation of soluble bromide to elemental bromine (Br$_2$), which was removed by distillation. Evaporation of the solvent produced a residue that contained HCl and radioisotopes of selenium (Se) and arsenic (As). After removing some of the HCl from the residue by repeatedly dissolving the residue in water and then evaporating the water, an aqueous acidic solution of the residue was prepared with a pH of about 1.4 (an acceptable range for the acidic solution is from about pH 0.5 to about pH 2.0). A suitable chelator was added which resulted a soluble chelation complex with $^{72}$Se (and other radioisotopes of selenium), which was selectively (>95%) extracted (along with the other selenium radioisotopes) by liquid-liquid extraction from the aqueous solution into a liquid organic phase. The liquid organic phase is a $^{72}$Se/$^{72}$As generator that includes chelation complexes of $^{72}$Se and other radioisotopes of selenium. The liquid organic phase was counted by gamma ray emission for the $^{72}$Se extraction yield. Arsenic-72 was re-extracted from the organic phase with a mineral acid acidified aqueous solution of oxalic acid (0.005-0.5 molL-1).

Having given a brief description of the $^{72}$Se/$^{72}$As generators of this invention, a more detailed description now follows. Chemical reagents used in preparation of embodiment generators were purchased from FISHER SCIENTIFIC, Pittsburgh, Pa., and were used without further purification. The water used for radioisotope preparations was deionized and purified using a Millipore system to greater than 18 MΩxcm). The pH adjustments were conducted with hydrochloric acid and sodium bicarbonate (NaHCO$_3$) unless otherwise stated. The encapsulated NaBr target was fabricated by MODDRELL MANUFACTURING MANAGEMENT, LLC. Target capsule halves were machined from INCONEL® 625, each having a window thickness of 0.3 mm. NaBr salt pucks were prepared by casting and then sealed inside the capsule under vacuum by means of electron beam welding.

Radioactive assays were determined by gamma-ray (γ-ray) spectrometry using an EG&G ORTEC Model GMX-35200-S HPGe detector system, and a CANBERRA Model 35-Plus multichannel analyzer. Radioisotope decay data were taken from a Table of Isotopes in Firestone et al, C. M. Table of Isotopes, 8th Edition, 1999 Update, Wiley, 1999. Simulated proton irradiations, which were used to predict residual radioisotope activities, have been described in Fassbender et al. "Proton beam simulation with MCNPX: Gallium metal activation estimates below 30 MeV relevant to the bulk production of $^{68}$Ge and $^{65}$Zn," Nuclear Instruments and Methods in Physics Research Section B: Beam Interactions with Materials and Atoms (2007), vol. 261, pp. 742-746.

Suitable target materials for this invention are alkali bromides because they are relatively inexpensive and biologically benign starting materials with sufficiently high yield for the production of $^{72}$Se. Solutions of these targets after irradiation are relatively easy to prepare because the alkali bromides are very soluble in water. Thus, suitable target materials for the method include alkali bromides such as sodium bromide, potassium bromide, rubidium bromide, and cesium bromide. Irradiation of these targets produces large amount of heat. A comparison of the thermal conductivities of alkali bromides NaBr, KBr, RbBr, and CsBr shows that NaBr can best accommodate heat transfer within the target due to irradiation. Thus, a preferred target material is NaBr.

Irradiation of a NaBr target took place at The Los Alamos National Laboratory Isotope Production Facility (LANL-IPF). This facility uses a target carrier assembly designed to position targets into three energy regions. The stack used for irradiation carried a NaBr target along with two other routine production targets. The NaBr target occupied the high energy slot, while two gallium targets in the medium and low energy slots utilized the degraded proton beam. Targets were mounted in target holders and held in the carrier assembly so that the target faces were separated by 5 mm thick cooling water channels. The NaBr target (51 grams of NaBr, 0.496 mol Br) was encased in an INCONEL shell and was irradiated for a period of 10 hours utilizing a nominal proton energy range of 92 MeV<$E_p$<72 MeV. A total electrical charge of 3.56 Coulombs (989 µAh) was delivered to the NaBr target. The detailed energy degradation in the individual target elements surrounding the NaBr target is provided in Table 1.

TABLE 1

| Position | Target element | Thickness (mg/cm$^2$) | Incident Energy (MeV) | Exit Energy (MeV) | Energy Loss (MeV) |
|---|---|---|---|---|---|
| 1 | INCONEL | 540.46 | 100.000 | 97.224 | 2.776 |
| 2 | water | 500.0 | 97.224 | 93.410 | 3.814 |
| 3 | INCONEL | 249.6 | 93.410 | 92.070 | 1.340 |
| 4 | NaBr | 3498.9 | 92.070 | 72.361 | 19.710 |
| 5 | INCONEL | 249.6 | 72.361 | 70.738 | 1.623 |
| 6 | water | 500.0 | 70.736 | 65.814 | 4.923 |

Energy loss calculations (column 6 from Table 1) are based upon formulas taken from: Andersen et al., Hydrogen stopping powers and ranges in all elements, Pergamon Press, 1977. A thermal analysis of the NaBr target (assuming a 250 µA beam current on the target) shows that the maximum temperature for the NaBr target remained below its melting point of 747° C.

A calculation was performed to predict the production yields of radioisotopes expected to be formed in the irradiation of a NaBr target for 10 hours at 100 µA. The results of the calculation are summarized in Table 2 below.

TABLE 2

| Element | A | Activity (Ci) | Activity (Bq) |
|---|---|---|---|
| Zn | 65 | $5.99 \times 10^{-6}$ | $2.22 \times 10^5$ |
| Be | 8 | $2.67 \times 10^{-5}$ | $9.86 \times 10^5$ |
| Ge | 68 | $3.24 \times 10^{-5}$ | $1.20 \times 10^6$ |
| H | 3 | $4.06 \times 10^{-5}$ | $1.50 \times 10^6$ |
| As | 80 | $2.13 \times 10^{-4}$ | $7.86 \times 10^6$ |
| Ga | 67 | $7.15 \times 10^{-4}$ | $2.65 \times 10^7$ |
| Br | 77m | $9.42 \times 10^{-4}$ | $3.48 \times 10^7$ |
| B | 12 | $1.69 \times 10^{-3}$ | $6.24 \times 10^7$ |
| Br | 73 | $1.69 \times 10^{-3}$ | $6.24 \times 10^7$ |
| Se | 70 | $1.69 \times 10^{-3}$ | $6.24 \times 10^7$ |
| Ga | 72 | $1.97 \times 10^{-3}$ | $7.27 \times 10^7$ |
| Ge | 75 | $3.35 \times 10^{-3}$ | $1.24 \times 10^8$ |
| O | 19 | $3.37 \times 10^{-3}$ | $1.25 \times 10^8$ |
| Se | 71 | $3.37 \times 10^{-3}$ | $1.25 \times 10^8$ |
| Kr | 74 | $3.37 \times 10^{-3}$ | $1.25 \times 10^8$ |
| C | 11 | $3.37 \times 10^{-3}$ | $1.25 \times 10^8$ |
| F | 22 | $5.00 \times 10^{-3}$ | $1.85 \times 10^8$ |
| As | 73 | $6.14 \times 10^{-3}$ | $2.27 \times 10^8$ |
| Ge | 69 | $7.13 \times 10^{-3}$ | $2.64 \times 10^8$ |
| Na | 22 | $8.96 \times 10^{-3}$ | $3.32 \times 10^8$ |
| Se | 72 | $9.23 \times 10^{-3}$ | $3.42 \times 10^8$ |
| Ge | 71 | $9.42 \times 10^{-3}$ | $3.49 \times 10^8$ |
| Se | 77m | $9.61 \times 10^{-3}$ | $3.56 \times 10^8$ |
| As | 70 | $1.01 \times 10^{-2}$ | $3.74 \times 10^8$ |
| N | 16 | $1.18 \times 10^{-2}$ | $4.37 \times 10^8$ |
| Se | 81m | $1.50 \times 10^{-2}$ | $5.54 \times 10^8$ |
| As | 74 | $1.95 \times 10^{-2}$ | $7.22 \times 10^8$ |
| Na | 24 | $1.99 \times 10^{-2}$ | $7.37 \times 10^8$ |
| Ga | 70 | $2.03 \times 10^{-2}$ | $7.49 \times 10^8$ |
| Na | 20 | $2.70 \times 10^{-2}$ | $9.99 \times 10^8$ |
| Se | 75 | $3.07 \times 10^{-2}$ | $1.14 \times 10^9$ |
| As | 77 | $3.27 \times 10^{-2}$ | $1.21 \times 10^9$ |
| Se | 81 | $4.03 \times 10^{-2}$ | $1.49 \times 10^9$ |
| As | 79 | $4.05 \times 10^{-2}$ | $1.50 \times 10^9$ |
| Ga | 68 | $5.05 \times 10^{-2}$ | $1.87 \times 10^9$ |
| Na | 24m | $5.31 \times 10^{-2}$ | $1.96 \times 10^9$ |
| Se | 79m | $6.02 \times 10^{-2}$ | $2.23 \times 10^9$ |
| N | 13 | $6.07 \times 10^{-2}$ | $2.25 \times 10^9$ |
| O | 15 | $7.09 \times 10^{-2}$ | $2.62 \times 10^9$ |
| As | 71 | $7.22 \times 10^{-2}$ | $2.67 \times 10^9$ |
| F | 21 | $8.83 \times 10^{-2}$ | $3.27 \times 10^9$ |
| Mg | 22 | $9.95 \times 10^{-2}$ | $3.68 \times 10^9$ |
| Kr | 75 | $1.16 \times 10^{-1}$ | $4.31 \times 10^9$ |
| Br | 74m | $1.23 \times 10^{-1}$ | $4.55 \times 10^9$ |
| Ne | 23 | $1.68 \times 10^{-1}$ | $6.22 \times 10^9$ |
| Ne | 19 | $1.86 \times 10^{-1}$ | $6.87 \times 10^9$ |
| Se | 73m | $2.14 \times 10^{-1}$ | $7.93 \times 10^9$ |
| Br | 82 | $2.73 \times 10^{-1}$ | $1.01 \times 10^{10}$ |
| As | 72 | $3.05 \times 10^{-1}$ | $1.13 \times 10^{10}$ |
| Na | 21 | $3.36 \times 10^{-1}$ | $1.24 \times 10^{10}$ |
| Br | 74 | $3.93 \times 10^{-1}$ | $1.45 \times 10^{10}$ |
| F | 20 | $4.90 \times 10^{-1}$ | $1.81 \times 10^{10}$ |
| Se | 73 | $5.69 \times 10^{-1}$ | $2.10 \times 10^{10}$ |
| Kr | 76 | $6.39 \times 10^{-1}$ | $2.36 \times 10^{10}$ |
| As | 76 | $6.54 \times 10^{-1}$ | $2.42 \times 10^{10}$ |
| Mg | 23 | $6.65 \times 10^{-1}$ | $2.46 \times 10^{10}$ |
| Kr | 79 | $9.24 \times 10^{-1}$ | $3.42 \times 10^{10}$ |
| As | 78 | 1.19 | $4.42 \times 10^{10}$ |
| Br | 80m | 1.25 | $4.63 \times 10^{10}$ |
| Br | 82m | 1.59 | $5.89 \times 10^{10}$ |
| F | 18 | 1.98 | $7.33 \times 10^{10}$ |
| Br | 77 | 2.69 | $9.94 \times 10^{10}$ |
| Br | 79m | 2.78 | $1.03 \times 10^{11}$ |
| Br | 76 | 5.56 | $2.06 \times 10^{11}$ |
| Kr | 77 | 5.97 | $2.21 \times 10^{11}$ |
| Br | 75 | 6.61 | $2.44 \times 10^{11}$ |
| Br | 80 | 8.77 | $3.25 \times 10^{11}$ |
| Br | 78 | $1.65 \times 10^1$ | $6.12 \times 10^{11}$ |

The total production yields of radioisotopes of interest at the end of bombardment (EOB) from the irradiation of NaBr were determined by the analysis of the measured gamma ray spectra of the primary counting sample. The primary counting sample was an untreated aliquot of an initial dissolution of the NaBr target, which is described later in this section. Gamma spectra for radioisotopes of interest were collected over a period of 35 days and half-lives. The half-life, $t_{1/2}$, and the activity at the end of bombardment, $A_0$, were determined from linear regression for all isotopes except $^{72}$Se. The observed $^{72}$Se production yield amounted to 81.3% of the expected value derived from experimental $^{nat}Br(p,x)^{72}Se$ reaction cross sections (see Faβbender et al. "The $^{nat}Br(p,x)^{73,75}Se$ nuclear processes: a convenient route for the production of radioselenium tracers relevant to amino acid labeling," Applied Radiation and Isotopes (2001), vol. 54, pp. 905-913). MCNPX activation estimates were obtained for all major radioisotopes. MCNPX, which stands for "Monte Carlo N-particle eXtended," is a general purpose Monte Carlo radiation transport code for modeling the interaction of radiation with everything. There was good agreement between predicted and measured values for $^{75}$Se. However, the Monte Carlo model underestimated $^{74}$As formation by a factor of two and $^{72}$Se formation by a factor of four.

Following irradiation, the target was packaged and shipped to the Los Alamos National Laboratory (LANL) Hot Cell Facility for radiochemical processing and chemical analysis. The irradiated target material was removed from the shielding container by remote handling in a hot cell. The target shell was inspected, and no visible burns were seen on the casing material. The target casing was perforated and target material was dissolved using successive washes of approximately 75 mL of water each. Greater than 99% of the activity was contained within the first two washes, which were combined to provide a volume of 150 mL. A. 50 mL aliquot from this volume of 150 mL was retained as a primary counting sample without any chemical processing. This 50 mL aliquot was periodically measured over a period of 35 days to determine activities and half-lives of the radioisotopes of interest. The remaining 100 mL was equally divided into four 25 mL aliquots. Three of these aliquots were treated as described below.

Soluble bromide (Br⁻) was quantitatively removed from three of the four aliquots by oxidation to elemental bromine, followed by distillation. Two methods were used to oxidize dissolved bromide to form bromine:

$$6NaBr + 8HNO_3 \leftrightarrows 3Br_2 \leftrightarrows 2NO\uparrow + 4H_2O + 6NaNO_3 \quad \text{Eq. 1}$$

$$2NaBr + 2HCl + H_2O_2 \leftrightarrows Br_2\uparrow + 2NaCl + 2H_2O \quad \text{Eq. 2}$$

In the first method, summarized by Eq. 1 above, 0.30 mol HNO₃ was used as the oxidizing agent. The second method, summarized by Eq. 2 above, used concentrated HCl (0.34 mol HCl) and a 30% solution of hydrogen/peroxide (0.167 mol H₂O₂) as the oxidizing agent. In the second method, the HCl was slowly added to the sample first, and then peroxide was added second. In both methods, the solution turned a red/orange color and bromine fumes were observed. The bromine was trapped in 10 N aqueous NaOH to prevent the spread of activated bromine gas through the ventilation system, The reaction vessel was attached to the distillation apparatus, and the reaction was stirred without heat for a period of 30 minutes. Following stirring, the solution was heated to remove the bromine completely by distillation and subsequently evaporated to dryness. Following distillation, the two traps and the sample vessel were counted using the above procedures to assess bromine capture and any loss of selenium or arsenic due to formation of volatile chloride salts.

Separation of $^{72}$Se from the acidic solution of the dissolved target was performed by chelation of the selenium into a chelation complex followed by solvent extraction of the chelation complex. A chelation complex is a chemical complex formed between a metal and a ligand wherein the metal is bonded to at least two atoms of the ligand. After removal of elemental bromine, the solid residues were re-dissolved in 20 mL of H₂O. After adjusting the pH of the resulting aqueous solution to a pH of 1.3 using HCl and NaHCO₃, a suitable chelator capable of forming a chelation complex with selenium was added. Suitable chelators are those that selectively form complexes with selenium, including $^{72}$Se. They include, but are not limited to, chelators selected from R—COOH (carboxylic acids), R—COO— (carboxylates, the conjugate bases of the carboxylic acids), dicarboxylic acids (oxalic acid, for example), conjugate bases of dicarboxylic acids (oxalate, for example),

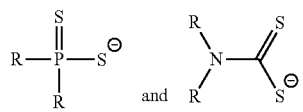

wherein R comprises an aliphatic group, an aromatic group, or combinations thereof. Some examples of these R groups include, but are not limited to, methyl, ethyl, propyl, butyl, pentyl, hexyl, phenyl, aryl, and substituted aryl. The chelator whose structure appears on the right above, i.e. (R)(R)NC(=S)(S) is more commonly known as a dithiocarbamate. Each of the structures shown has multiple heteroatoms. Each is a chelator because multiple heteroatoms (for example, two oxygen atoms from a carboxylic acid, or two sulfur atoms from a dithiocarbamate) form bonds to one selenium. After adjusting the pH to a pH of 1.3, as described above, 100-200 mg (0.58 to 1.17 mmol) of sodium diethyldithiocarbamate was added and the resulting solution was stirred for 5 min, and then an equal volume of ethylacetate (pre-equilibrated with H₂O) was added and the resulting mixture was stirred for an additional 30 min. The aqueous and organic phases were counted using an HPGe-γ-ray detector, and the distribution ratios of Se and As were determined. The 20 mL organic phase was periodically extracted with an equal volume of water containing 1 mmol of sodium diethyldithiocarbamate via vigorous stirring for 5 minutes, adjusted to a pH of 1.3. The distribution of $^{72}$Se (parent) and $^{72}$As (daughter) was then measured for each batch extraction.

A liquid-liquid extraction was performed to extract a chelation complex of $^{72}$Se from an aqueous acidic solution in order to provide a chelation-based $^{72}$Se/$^{72}$As radioisotope generator system. Suitable organic phases for the liquid-liquid extraction include non-polar or polar organic liquids that are not miscible with water. Some non-limiting examples of suitable organic phases include, but are not limited to, 1,4-dioxane, diethyl ether, tert-butyl methyl ether, a pentane, a hexane, a cyclohexane, an ester, tetrahydrofuran, an alcohol, and suitable combinations. Some non-limiting examples of suitable alcohols include a butanol and a pentanol. Some non-limiting examples of suitable esters include ethyl acetate, ethyl formate, methyl propionate, ethyl propionate butyl propionate, methyl formate, and methyl benzoate. Ethyl acetate is a preferred organic phase.

The $^{72}$Se activity could not be measured directly because the 45 keV γ-line associated with the decay of $^{72}$Se was below the calibration limit for the available HPGe detector. The $^{72}$As activity was determined indirectly by monitoring the in-growth of the $^{72}$As daughter and assuming a transient equilibrium between the two isotopes. Such indirectly measured $^{72}$Se activity agreed well with calculated values over a 35 day period. The direct production yield of $^{72}$As could not determined because the time elapsed from the end of bombardment to the initial gamma ray measurement was of the order of 3-4 half-lives. This was also the case for $^{73}$Se produced during the irradiation.

Chemical separation yields were determined from the aliquots after treatment with oxidizing agent (e.g. hydrogen peroxide) and removal of elemental bromine. Chemical processing in the presence of excess HCl, which quantitatively reduced any Se(VI), ensured that all Se in solution was converted to Se(IV) (see: Saygi et al., "Speciation of selenium (IV) and selenium(VI) in environmental samples by the combination of graphite furnace atomic absorption spectrometric determination and solid phase extraction on Dianion HP-2MG," Talanta (2007), vol. 71, pp. 1375-1381). Longer-lived $^{75}$Se ($t_{1/2}$=119 days) was used as a tracer for the selenium isotopes, while $^{72}$As and $^{74}$As were used to trace arsenic. The chemical separation yield of the initial selenium recovery from the aliquots amounted to about 94%. About 95% of the directly formed radioarsenic, i.e. via nuclear reaction with protons, as evident by the presence of $^{74}$As, remained in the aqueous phase.

Liquid-liquid distribution coefficients of tetravalent selenium and pentavalent arsenic in a diethyldithiocarbamate/tributyl phosphate system suggest that a two-phase separation system for the two elements may be feasible. For the tributyl phosphate (TBP) system, $K_D$=2.09 was determined for chelated Se(IV) at pH=1.0 (see: see: Saygi et al., "Speciation of selenium(IV) and selenium(VI) in environmental samples by the combination of graphite furnace atomic absorption spectrometric determination and solid phase extraction on Dianion HP-2MG," Talanta (2007), vol. 71, pp. 1375-1381). We conducted a similar separation replacing the highly toxic TBP with the milder ethylacetate, which has a similar polarity and was anticipated to yield similar effectiveness for extraction. In fact, the $K_D$ determined in this corresponding system was measured to be 2.04 at pH=1.3. Sodium diethyl dithiocarbamate was added to provide a dithiocarbamate chelator for extracting the selenium into the organic phase. The parent isotope $^{72}$Se remains in the organic phase while the $^{72}$As daughter can be repeatedly extracted into the aqueous phase.

The $^{72}$Se containing generator phase was repeatedly allowed to accumulate $^{72}$As daughter activity, and decay-generated $^{72}$As was periodically re-extracted into aqueous phases to determine parent "break-through", i.e., $^{72}$Se removal from the organic phase, and daughter extraction yield, i.e., $^{72}$As recovery. Such an aqueous phase consisted of a solution of another chelator, for example, an acidified carboxylic acid. An aqueous phase with oxalic acid, for example, was used. The $^{72}$Se "break-through" amounted to (0.9±0.05)% of the $^{72}$Se activity load at the beginning of each extraction. 76±0.7% of the decay generated $^{72}$As activity could be re-extracted into the aqueous phase.

Wenclawiak et al. reported that As(III) is much more strongly coordinated by dithiocarbamates than As(V) (see: Wenclawiak et al., "Studies on bulky residual group substituted arsenic (III) dithioearbamate structures," Inorg. Chim. Acta., May 2003, vol. 348, pp. 1-7). Thus, it was expected that As(V) would have a lower organic/aqueous distribution coefficient than As(III). Generator yield performance may depend on the As(V)/As(III) ratio. $^{72}$As remaining in the organic layer will likely be As(III). Table 3 below gives a summary of relevant parameters.

TABLE 3

| | |
|---|---|
| Selenium-72 production yield NaBr(p, x) | 0.03 mCi/μAh |
| Selenium-75 co-formation NaBr(p, x) | 0.04 mCi/μAh |

TABLE 3-continued

| | |
|---|---|
| Initial $^{72}$Se chemical recovery yield from target matrix | (94 ± 2)% |
| Arsenic-72 generator liquid-liquid extraction batch yield | (76 ± 0.7)% |
| Selenium-72 liquid-liquid extraction "break-through" | (0.9 ± 0.05)% |

The present invention is also concerned with a generator having two phases wherein one of the phases is immobilized (i.e. one of the phases is solid). An embodiment solid phase extraction system may be a desktop $^{72}$As generator system. This embodiment includes a mobile liquid extraction phase and a solid phase wherein $^{72}$Se is sorbed on the solid phase via chelation while the $^{72}$As daughter is continuously removed via a mobile liquid extraction phase owing to the lower stability of As(V) chelate as compared to Se(IV).

A benefit of the $^{72}$Se/$^{72}$As generator of this invention is that $^{72}$As may be conveniently extracted multiple times form the liquid organic phase into an aqueous acidic phase at pH 1.4 Thus, researchers and clinicians are provided with a solution containing $^{72}$Se, and thus with a convenient source of $^{72}$As for further applications. Another advantage is that $^{72}$As is provided at the site where PET is performed. $^{72}$As may be repetitively extracted from the generator, which can be re-used by simply allowing time for the $^{72}$As to form after each extraction. The useful life of the generator depends on the half-life of $^{72}$Se (about 8.5 days) rather than on the half-life of $^{72}$As (about 26.5 hours). Others have mentioned that based on the $t_{1/2}$, if the generator is prepared off-site, it could be shipped about every four weeks to the location where the $^{72}$As is used. Alternatively, the irradiated NaBr target could be shipped to the location and the generator could be prepared from the target at that location. The generator provides a reliable source of $^{72}$As that safe with respect to radiation and easy to use.

In summary, a $^{72}$Se/$^{72}$As generator has been prepared using chelation of selenium followed by extraction of the chelated selenium liquid-liquid extraction. The initial recovery yield for the $^{72}$Se parent from a dissolved target matrix was 94%. The generator, i.e. the liquid organic phase, was periodically subjected to $^{72}$As daughter re-extraction. More than 76% of the decay-formed $^{72}$As could be removed from the generator, accompanied by 0.9% of the $^{72}$Se load. The generator, as well as a solid phase generator prepared by immobilization of chelated $^{72}$Se on a suitable solid carrier phase, allow for repeated removal of generated $^{72}$As for radio-labeling purposes. These $^{72}$Se/$^{72}$As generators may lead to more widespread use of $^{72}$As for PET scanning.

Although the present invention has been described with reference to specific details, it is not intended that such details should be regarded as limitations upon the scope of the invention, except as and to the extent that they are included in the accompanying claims.

What is claimed is:

1. A method for preparing a $^{72}$Se/$^{72}$As generator, comprising
    forming an aqueous acidic solution of an irradiated target of an alkali bromide, the aqueous acidic solution comprising hydrogen chloride and soluble bromide and water solvent, the irradiated target comprising radioisotopes of selenium that include $^{72}$Se,
    oxidizing the soluble bromide to elemental bromine,
    removing the elemental bromine from the solution,
    evaporating the water solvent to provide a residue,
    forming an acidic aqueous solution of the residue, the acidic aqueous solution comprising a chelator suitable for forming a soluble chelation complex with $^{72}$Se,
    extracting the soluble chelation complex with $^{72}$Se from the acidic aqueous solution into a liquid organic phase not miscible with the acidic aqueous solution, thereby preparing $^{72}$Se/$^{72}$As generator.

2. The method of claim 1, further comprising the step of irradiating an alkali bromide target with protons under conditions suitable for the production of $^{72}$Se.

3. The method of claim 1, wherein the alkali bromide target comprises sodium bromide.

4. The method of claim 1, wherein the organic phase that is not miscible with the acidic aqueous solution comprises a liquid organic phase.

5. The method of claim 4, wherein the liquid organic phase comprises a compound selected from 1,4-dioxane, diethyl ether, tert-butyl methyl ether, a hexane, a cyclohexane, an ester, tetrahydrofuran, and an alcohol.

6. The method of claim 5, wherein the ester is selected from ethyl acetate, ethyl formate, methyl propionate, ethyl propionate, butyl propionate, methyl formate, methyl benzoate, and wherein the alcohol is selected from a butanol and a pentanol.

7. The method of claim 5, wherein the liquid organic phase comprises ethyl acetate.

8. The method of clam 1, acidic aqueous solution of the residue comprises a pH from about pH 0.5 to about pH 2.0.

9. The method of claim 1, wherein the chelator is selected from R—COOH, R—COO—, a di-carboxylic acid, a conjugate base of a di-carboxylic acid,

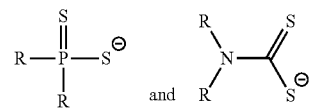

wherein R comprises an aliphatic group, an aromatic group, or combinations thereof.

10. The method of claim 9, wherein R is selected independently from methyl, ethyl, propyl, butyl, pentyl, hexyl, phenyl, aryl, and substituted aryl.

11. The method of claim 9, wherein the chelator is a dithiocarbamate.

12. The method of claim 9, wherein the chelator is selected from oxalic acid and oxalate.

13. A method for producing $^{72}$As, comprising:
    forming an aqueous acidic solution of an irradiated target of an alkali bromide, the aqueous acidic solution comprising hydrogen chloride and soluble bromide and water solvent, the irradiated target comprising radioisotopes of selenium that include $^{72}$Se,
    oxidizing the soluble bromide to elemental bromine,
    removing the elemental bromine from the solution,
    evaporating the water solvent to provide a residue,
    forming an acidic aqueous solution of the residue, the acidic aqueous solution comprising a chelator suitable for forming a soluble chelation complex with $^{72}$Se,
    extracting the soluble chelation complex with $^{72}$Se from the acidic aqueous solution into liquid organic phase not miscible with the acidic aqueous solution, the liquid organic phase comprising a $^{72}$Se/$^{72}$As generator, and
    extracting $^{72}$As from the $^{72}$Se/$^{72}$As generator into an aqueous phase that includes a soluble chelator and contacting this aqueous solution with an anion exchanger to remove selenium from this aqueous phase.

14. A $^{72}$Se/$^{72}$As generator, comprising a soluble complex of $^{72}$Se bonded to a chelator in an organic phase, the chelator selected from R—COOH, R—COO⁻, a dicarboxylic acid, a conjugate base of a dicarboxylic acid,

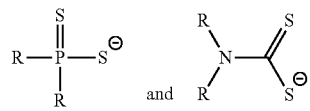

wherein R comprises an aliphatic group, an aromatic group, or combinations thereof.

15. The generator of claim 14, wherein R is an aliphatic group or selected independently from methyl, ethyl, propyl, butyl, pentyl, hexyl, phenyl, aryl, and substituted aryl.

16. The generator of claim 14, wherein the organic phase is selected from 1,4-dioxane, diethyl ether, tert-butyl methyl ether, a hexane, a cyclohexane, an ester, tetrahydrofuran, and an alcohol not miscible with water.

17. The generator of claim 16, wherein the ester is selected from ethyl acetate, ethyl formate, methyl propionate, ethyl propionate, butyl propionate, methyl formate, and methyl benzoate.

18. The generator of claim 17, wherein the ester is ethyl acetate.

19. The generator of claim 14, wherein the dicarboxylic acid is oxalic acid and the conjugate base of the dicarboxylic acid is oxalate.

* * * * *